(12) United States Patent
Blackmore

(10) Patent No.: US 6,280,446 B1
(45) Date of Patent: Aug. 28, 2001

(54) TUBULAR SPLINT

(76) Inventor: Armand N. Blackmore, 5572 Gaertner Ct., Bay City, MI (US) 48706

( * ) Notice: Subject to any disclaimer, the term of this patent is extended or adjusted under 35 U.S.C. 154(b) by 0 days.

(21) Appl. No.: 09/429,356

(22) Filed: Oct. 28, 1999

(51) Int. Cl.[7] .................................................. A61B 17/00
(52) U.S. Cl. .................................................................. 606/74
(58) Field of Search ............................... 606/56, 72, 74; 602/5, 6, 12, 16, 20, 23, 25

(56) References Cited

U.S. PATENT DOCUMENTS

| | | |
|---|---|---|
| 1,156,440 | 10/1915 | Smith . |
| 1,950,799 | 3/1934 | Jones . |
| 2,110,414 | 3/1938 | Bell . |
| 2,502,902 | 4/1950 | Tofflemire . |
| 2,966,907 | 1/1961 | Fasolino . |
| 3,900,025 | 8/1975 | Barnes, Jr. . |
| 4,263,904 | 4/1981 | Judet . |
| 4,890,631 * | 1/1990 | Hardy ..................................... 606/59 |
| 5,020,797 * | 6/1991 | Burns ..................................... 272/143 |
| 5,108,393 * | 4/1992 | Ruffa ..................................... 606/56 |
| 5,190,545 | 3/1993 | Corsi et al. . |
| 5,443,483 | 8/1995 | Kirsch . |
| 5,662,653 * | 9/1997 | Songer et al. ..................... 606/61 |
| 5,665,089 | 9/1997 | Dall et al. . |
| 5,741,259 | 4/1998 | Chan . |
| 5,810,816 * | 9/1998 | Roussouly et al. ................ 606/61 |
| 5,810,817 * | 9/1998 | Roussouly et al. ................ 606/61 |
| 5,810,824 | 9/1998 | Chan . |

FOREIGN PATENT DOCUMENTS 3244680 2/1982 (DE) .

* cited by examiner

*Primary Examiner*—Gene Mancene
*Assistant Examiner*—Eduardo C. Robert
(74) *Attorney, Agent, or Firm*—Reising, Ethington, Barnes, Kisselle, Learman & McCulloch, P.C.

(57) ABSTRACT

The tubular splint has a tubular shell with a slot extending from one end to the other. A first clamp bracket with a plurality of bores is fixed to the tubular shell adjacent to a first side of the slot. A second clamp bracket, with a plurality of threaded bores that are in substantially axial alignment with the plurality of bores in the first clamp bracket, is fixed to the tubular shell adjacent to a second side of the slot. A screw passes through each bore and screws into one of the plurality of threaded bores. A worm is journaled on one of the clamp brackets, engages a worm wheel on each screw and rotates all of the screws simultaneously. A wedge member can be secured to the bone and engaged by the shell.

15 Claims, 4 Drawing Sheets

TUBULAR SPLINT

FIELD OF THE INVENTION

This invention relates to a tubular splint and more particularly to a splint for large bones of the human body. The splint clamps to and encircles outer surfaces of bones and transmits force in a direction parallel to the axis of a bone.

BACKGROUND OF THE INVENTION

Large bones of the human body such as, for example, the femur, humerus, ulna and tibia are occasionally broken as a result of accidents or violent actions. A simple break can be straightened, encased in an external cast and then allowed to grow back together.

A more traumatic break which separates a large bone into three or more pieces may require surgery and the insertion of plates and multiple screws to secure each piece of the bone and hold the pieces in alignment with each other while they grow back together. The plate and screws may remain in place or they may be removed at a later date. Another splint that is used for bones broken in two or more pieces has pins that pass through the skin and engage the bone pieces. These pins are then secured to an outside holder that holds the bone pieces in fixed positions relative to each other while they grow back together.

Extremely traumatic breaks in large bones may result in substantial portions of bone being lost. Such traumatic breaks can be caused, for example, by a bullet that carries bone fragments through an exit wound while causing relatively minor soft tissue damage. When substantial bone material is lost, an orthopedic surgeon has limited options. He may be able to shorten the bone somewhat, a section of bone from a donor may be added if a suitable donor bone is available, or the extremity may be amputated.

Large bones may also be damaged when an artificial joint fails and must be removed. Quite often an extremity is shortened each time a new artificial joint is implanted. Surgeons often have no alternative to shortening an arm or leg when an artificial joint fails.

SUMMARY OF THE INVENTION

The splint is a tubular member with a slot extending its full length. A clamp bracket is secured to the tubular member on each side of the slot. Two screws pass through screw bores in each end of one of the clamp brackets and screw into threaded bores in the other clamp bracket. Each of the screws has a threaded shank portion, a worm wheel and a head. The head has a shoulder and a tool engaging structure. The tool engaging structure can be a slot for a screwdriver, a bore for a tool such as an Allan wrench, or a radially outer surface engagable by an appropriate tool.

A long worm is journaled in a worm bore that is perpendicular to the screw bores through one of the clamp brackets and engages the worm wheels on all of the screws. A head on the long worm is axially positioned in the worm bore between a bearing surface and a snap ring. Rotation of the long worm by an appropriate tool rotates all of the screws together. By rotating all of the screws together, equal reduction in bone diameter is attained on both ends of the tubular splint. The equal reduction in bore diameter provides holding force between the splint and bone that is nearly the same at both ends of the splint.

Apertures are provided in the walls of the tubular splint for the introduction of a bone adhesive or a bone building material. These materials are pumped through the apertures under pressure. Substantially all of the voids within the splint are filled with adhesive or the bone building material. These materials are, however, able to escape through the slot in the splint thereby insuring that the pressure exerted by materials injected into the splint is not too high.

The body of the tubular splint is a relatively thin material that can conform to the shape of the outer surface of a bone when the splint is used on a bone that is not cylindrical.

The circumference of some bones increases near their ends and joints. This change in circumference is accommodated by placing a ring on the bone that is received in the splint. The ring has a conical surface that engages the bone and a cylindrical surface that engages the splint.

The tubular splint is a strong structural member that increases the strength of a bone as well as holding bone parts in alignment. Even after a broken bone has grown back together and healed, the splint adds strength to the bone.

Artificial joints such as hip joints are attached on the inside of the bones. The tubular splint strengthens the connection between an artificial joint and a bone. In many cases the splint makes it possible to replace an artificial joint without shortening the length of a bone.

A person who receives the tubular splint can start using the extremity with the tubular splint within a few hours to a few days of the splint's insertion. The splint can transfer force as soon as it is tightened on the bone. Use of the bone with a splint is therefore limited only by healing of the incision and surrounding soft tissues.

BRIEF DESCRIPTION OF THE DRAWINGS

The presently preferred embodiment of the invention is disclosed in the following description and in the accompanying drawings, wherein.

DETAILED DESCRIPTION OF THE PREFERRED EMBODIMENT

Figure 1:
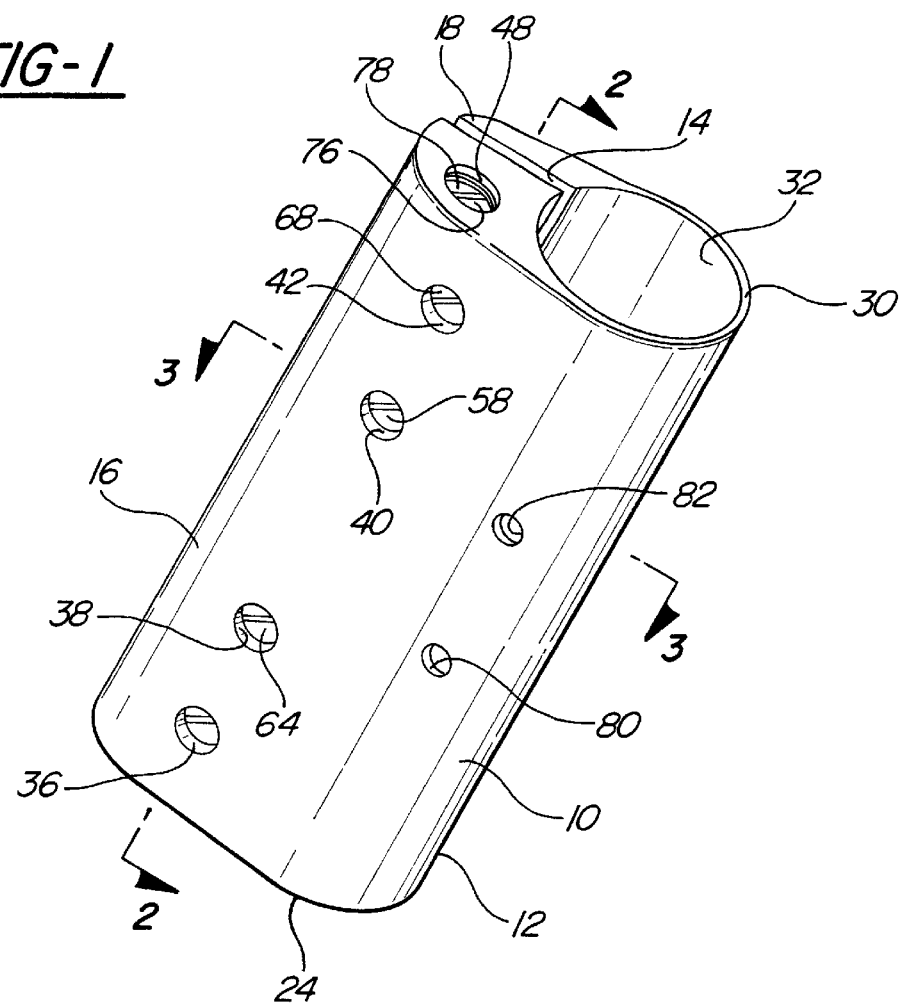
FIG. 1 is a perspective view of the splint.

The tubular splint 10 has a tubular shell 12 with a slot 14. The shell 12 is made from a flexible material such as stainless steel. The slot 14 can be widened to the point that the shell 12 can be slipped over a bone and then released to spring back to its original shape and encircle a bone. A first clamp bracket 16 and a second clamp bracket 18 are integral with the shell 12. The first clamp bracket 16 extends the length of the tubular splint 10 on one side of the slot 14. The second clamp bracket 18 extends the length of the splint 10 on the other side of the slot 14.

The first and second clamp brackets 16 and 18 are integral with a tubular shell 12 as stated above. However, if desired, the first and second clamp brackets 16 and 18 could be separate members that are secured to the tubular member by welding, mechanical fasteners or some other attaching system.

The second clamp bracket 18 has two threaded bores 20 and 22 near one end 24 and two threaded bores 26 and 28 near the other end 30. These threaded bores 20, 22, 26 and 28 are spaced from the inside surface 32 of the tubular shell 12 a short distance. Each of the threaded bores 20, 22, 26 and 28 has an axis that is parallel to a tangent to the inside surface 32.

The first clamp bracket 16 has four bores 36, 38, 40 and 42. Each of the four bores 36–42 is in substantial axial alignment with one of the threaded bores 20, 22, 26 or 28. A bearing surface 44 is provided in each bore 36–42 that is perpendicular to the bore axis and faces away from the adjacent threaded bore 20, 22, 26 or 28.

A worm bore 46, in the first clamp bracket 16, extends the entire length of the first clamp bracket. A worm axis of the worm bore 46 is in a plane that is perpendicular to the axes of the bores 36–42. The worm bore 46 has a large diameter cylindrical end 48 with a transverse bearing surface 50. A snap ring groove 52 is machined into the large diameter cylindrical end 48. A center portion 54 of the bore 46 has an intermediate diameter. A small diameter portion 56 of the worm bore 46 is on the opposite end of the worm bore from the large diameter cylindrical end 48.

A screw 58 passes through each bore 36–42 and screws into the aligned threaded bore 20, 22, 26 or 28. Each of the screws 58 has a threaded shank portion 60, a worm wheel 62 and a head 64. The head 64 has a shoulder 66 that engages the bearing surface 44 in the bore 36, 38, 40 or 42 and slides on the bearing surface when the screw 58 is rotated to reduce or increase the width of the slot 14. A slot 68 is provided in the head 64 for rotating the screw 58 with a screwdriver. Tool engaging structure other than the slot 68 can be provided if desired.

A worm 70 has a small diameter worm end 72 that is journaled in the small diameter portion 56 of the worm bore 46. A worm gear portion 74 of the worm 70 engages the worm wheel 62 on each screw 58. A worm head 76 of the worm 70 is journaled in the large diameter cylindrical end 48 of the worm bore 46. The worm head 76 is axially fixed between the transverse bearing surface 50 and a snap ring 78 in the snap ring groove 52. A slot 79 or other tool engaging structure is provided on the worm head 76.

Vent apertures 80 and 82 are provided in the tubular shell 12 as required. A bone adhesive or a bone building material can be pumped into the shell 12, through one of the vent apertures 80 or 82, and fill voids in the shell between the inside surface 32 and the bone or bone parts. Air can escape from inside the shells through the slot 14 or through the other vent aperture 80 or 82. It is also possible to insert bone adhesive or bone building material through the slot 14 if the slot is not closed.

A tubular splint 10 is selected for use which has the required length and diameter. The first clamp bracket 16 and the second clamp bracket 18 are separated and the tubular shell 12 is inserted around a bone or bone ends that require a splint 10. The first and second clamp brackets 16 and 18 are then permitted to spring back together and encase the bone. Screws 58 are then inserted into each of the bores 36–42 and screwed into the adjacent threaded bores 20, 22, 26 and 28. The screws 58 are tightened until the tubular shell 12 contacts and starts to apply pressure to the bone. The worm 70 is then inserted into the worm bore 46 and rotated until a worm head 76 engages the transverse bearing surface 50 in the worm bore 46. Prior to contact between the worm head 76 and the transverse bearing surface 50, rotation of the worm 70 causes the worm gear portion 74 to engage teeth on the worm wheel 62. Continued rotation of the worm 70 advances the worm into or out of the worm bore 46 depending upon the direction of rotation. A worm 70 does not rotate the worm wheels 62 until a worm is fully inserted into the worm bore 46. Once the worm head 76 engages the transverse surface 50, the snap ring 78 is seated in the snap ring groove 52. Rotation of the worm 70 after it is axially fixed rotates all of the worm wheels 62 together to tighten the screws 58 and close the slot 14 or to loosen the screws and open the slot 14 depending upon the direction of rotation. Rotating all of the screws 58 together keeps all the screws at about the same tension and prevents overtightening of one screw. The worm 70 and the worm wheels 62 also make simultaneous adjustment of all the screws 58 possible from a single location.

Figure 2:
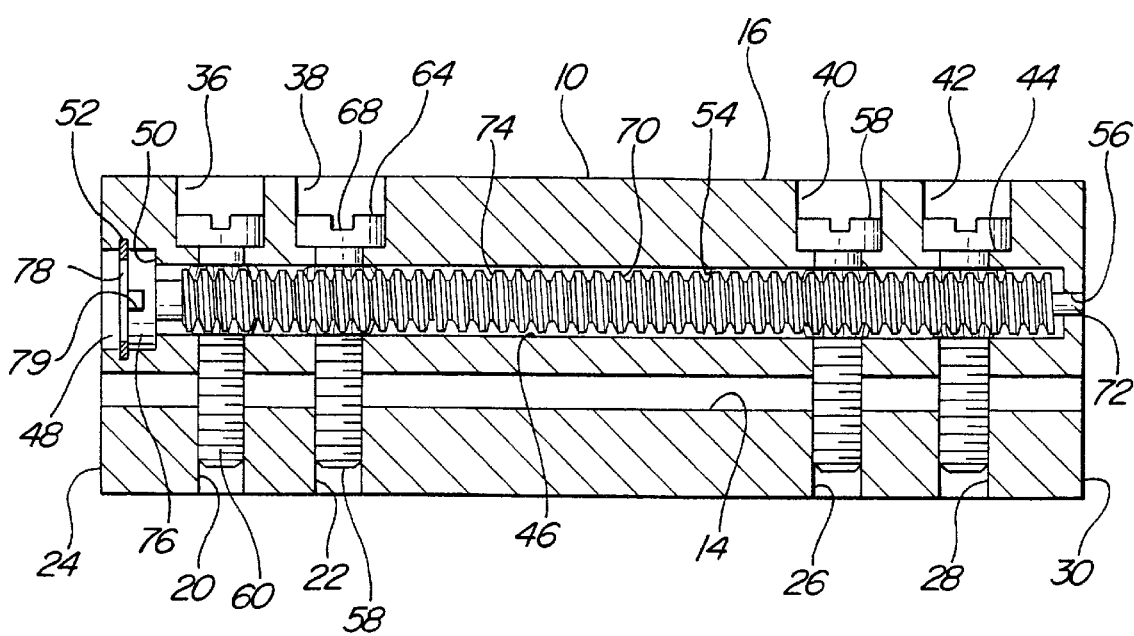
FIG. 2 is an enlarged sectional view taken along line 2—2 in FIG. 1.
Figure 3:
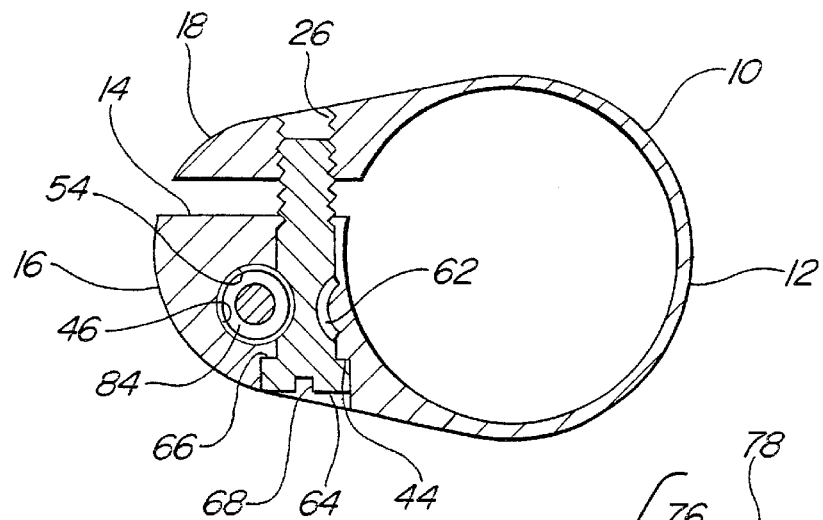
FIG. 3 is an enlarged sectional view taken along line 3—3 in FIG. 1.
Figure 4:
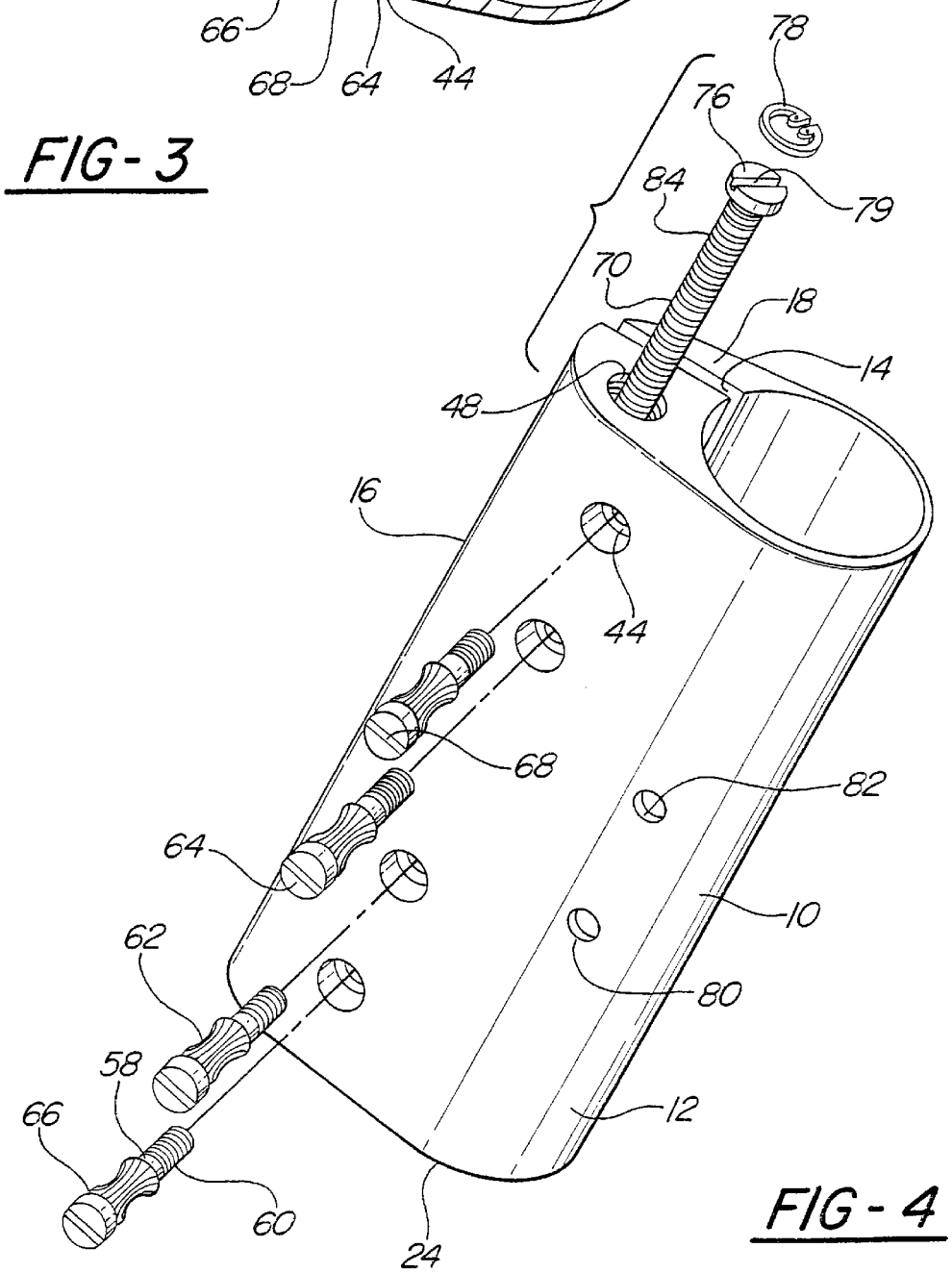
FIG. 4 is an expanded perspective view of the splint.

The worm 70 is relatively long. Inserting the worm 70 into the worm bore 46 inside an incision may be impossible. By removing the worm lands 84 from the worm gear portion 74 of the worm 70 in areas on the right side of each worm wheel 62, as shown in FIG. 2, the snap ring 78 can be removed and the worm 70 can be withdrawn from engagement with the worm wheels 62. A very short distance movement of the worm 70 is all that is required to disengage the worm from the worm wheels 62.

The tubular shell 12 has sufficient flexibility to conform to the shape of a bone with a cross section that is not round.

Figure 5:
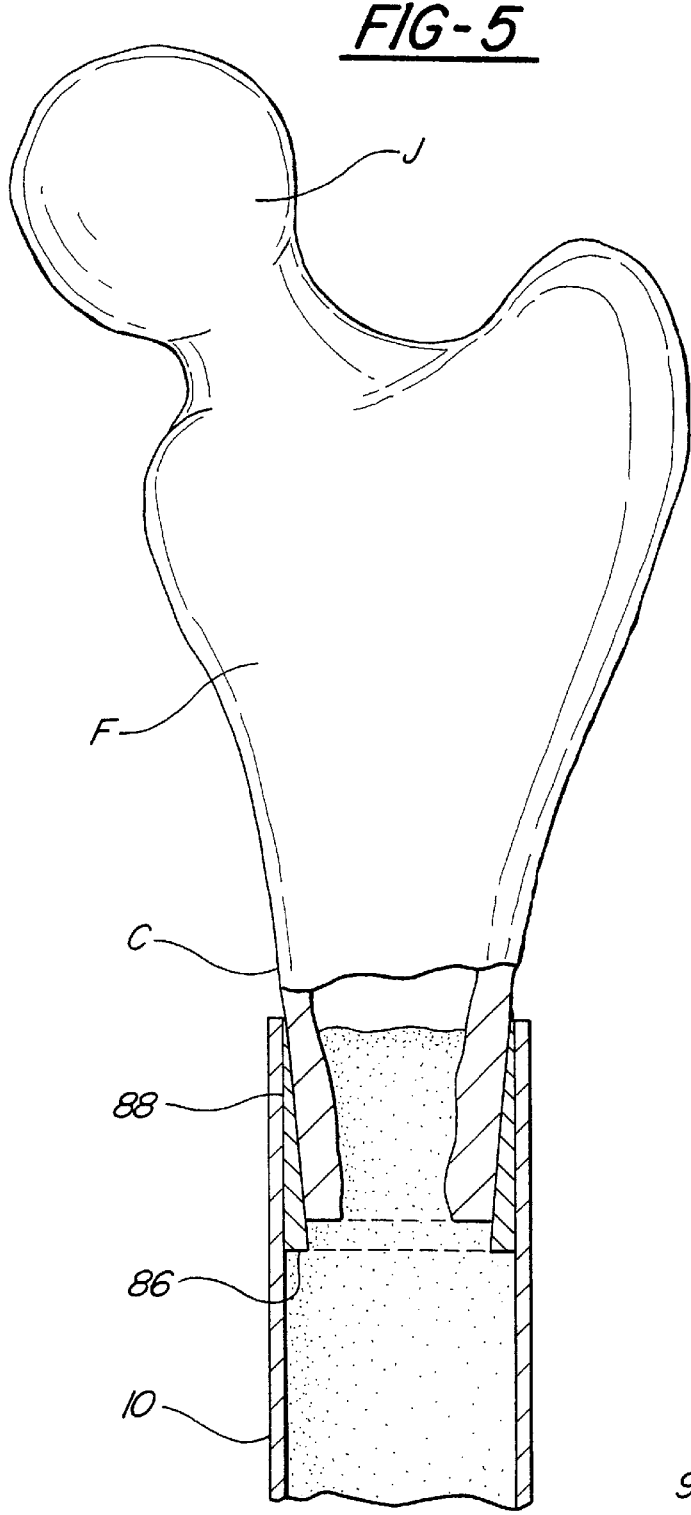
FIG. 5 is a sectional view of one end of the splint showing the employment of a sleeve for clamping the splint to a conical bone surface.
Figure 6:
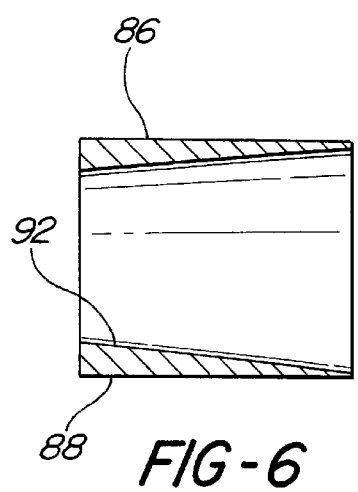
FIG. 6 is a sectional view of the sleeve.
Figure 7:
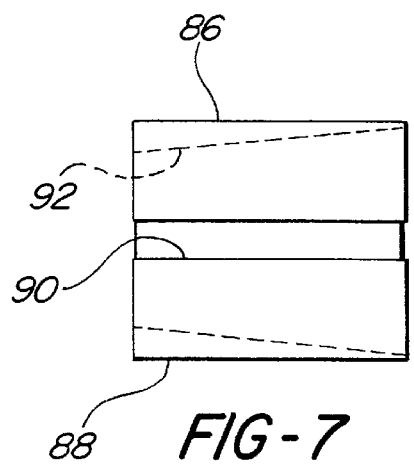
FIG. 7 is a side elevational view of the sleeve.
Figure 8:
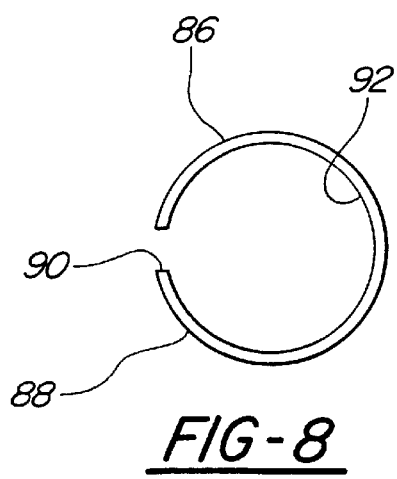
FIG. 8 is an end view of the sleeve.
Figure 9:
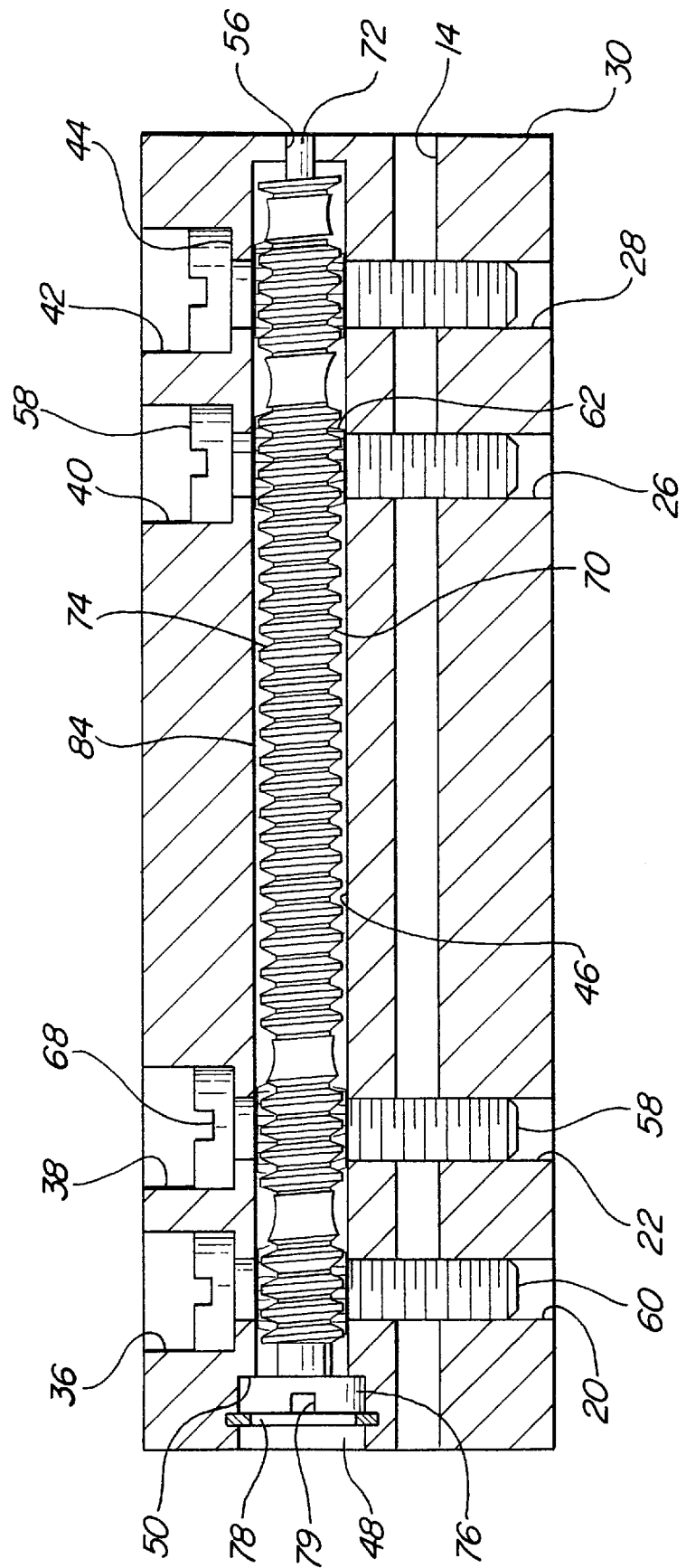
FIG. 9 is a sectional view similar to FIG. 2 with a modified worm.

Some bones have portions near a joint that are generally conical rather than cylindrical. The femur F near the hip joint J shown in FIG. 5 is generally conical. A tubular wedge 86 with a cylindrical outer surface 88, a conical inner surface 92 and a wedge slot 90 is slipped over the conical section C of the bone F. (note that lower portions of the femur are not shown in FIG. 5) The tubular wedge 86 provides a conical inner surface 92 that engages the bone F and a cylindrical outer surface 88 that is engaged by the tubular splint 10. These tubular wedges 86 are provided with a number of outside diameters and conical inner surfaces 92 with different angles relative to the tubular wedge centerline to accommodate various bone sizes and shapes.

Tubular wedges 86 can also be employed on the portion of a bone in one of the ends of the tubular shell 12 that is significantly smaller in diameter than the portion of the bone in the other end of the tubular shell. By equalizing the diameters of the tubular shell 12 at both ends of the tubular shell, the width of the slot 14 can be minimized.

Upon completion of clamping the tubular splint 10 to a bone, or two bone ends, the bone and the splint are capable of supporting loads. The tubular splint can hold axial loads as well as bending loads. Limitations on use of the bone will be due to the incision in the soft tissue and not to the strength of the splint 10 and the bone. However strength of the bone will in most cases increase over a period of time following insertion of the splint 10.

The disclosed embodiment is representative of a presently preferred form of the invention, but is intended to be illustrative rather than definitive thereof. The invention is defined in the claims.

I claim:

1. A tubular splint comprising:
   a tubular shell having a first end, a second end, means for receiving a bone, said means extending from the first end to the second end and a shell slot extending from the first end to the second end;

a first clamp bracket on said tubular shell adjacent to a first side of the shell slot, and a plurality of bores through the first clamp bracket spaced along a line extending from the first end to the second end of said tubular shell;

a second clamp bracket on said tubular shell adjacent to a second side of the shell slot, and a plurality of threaded bores in the second clamp bracket each of which is in axial alignment with one of the plurality of bores through the first clamp bracket; and a plurality of screws each of which passes through one of the plurality of bores through the first clamp bracket and screws into one of the plurality of threaded bores in the second clamp bracket.

2. A tubular splint, as set forth in claim 1, including a worm wheel secured to each of the plurality of screws; and
a worm journaled on the first clamp bracket and in mesh with all of the worm wheels.

3. A tubular splint, as set forth in claim 2, wherein the worm is journaled in a worm bore in the first clamp bracket and is axially fixed in the worm bore.

4. A tubular splint, as set forth in claim 3, including a snap ring mounted in a snap ring groove in the worm bore that limits axial movement of the worm in the worm bore.

5. A tubular splint, as set forth in claim 1, including a passage through said tubular shell for injecting a fluid into the tubular shell.

6. A tubular splint as set forth in claim 1, including a tubular wedge with a wedge slot, an inside sleeve surface that generally conforms to the shape of a bone and an outside sleeve surface that is engagable by said tubular shell.

7. A tubular splint, as set forth in claim 1, wherein the first clamp bracket and the second clamp bracket are fixed to the tubular shell.

8. A tubular splint, as set forth in claim 1, wherein the first clamp bracket and the second clamp bracket are both integral with the tubular shell.

9. A tubular splint comprising:
a tubular shell having a first end, a second end and a shell slot extending from the first end to the second end;
a first clamp bracket integral with said tubular shell and adjacent to a first side of the shell slot and a plurality of bores through the first clamp bracket;
a second clamp bracket integral with said tubular shell and adjacent to a second side of the shell slot, and a plurality of threaded bores through the second clamp bracket each of which is in axial alignment with one of the plurality of bores through the first clamp bracket;
a plurality of screws each of which passes through one of the plurality of bores through the first clamp bracket and screws into one of the plurality of threaded bores through the second clamp bracket;
a worm wheel secured to each of the plurality of screws;
a worm journaled on the first clamp bracket and in mesh with all of the worm wheels; and
a retainer mounted on the first clamp bracket which limits axial movement of the worm relative to the first clamp bracket.

10. A tubular splint, as set forth in claim 9, wherein the plurality of screws includes at least four screws.

11. A method of splinting a bone employing a tubular shell having a first end, a second end, a shell slot extending from the first end to the second end, a first clamp bracket integral with the tubular shell and adjacent to a first side of the shell slot, and a second clamp bracket integral with the tubular shell and adjacent to a second side of the shell slot comprising:
selecting said tubular shell with a shell length and a shell diameter that is appropriate for the bone to receive the splint;

separating the first clamp bracket from the second clamp bracket;

positioning the tubular shell adjacent to the bone;

releasing the first clamp bracket and the second clamp bracket to move toward each other and encircle the bone:

passing each of a plurality of screws through a bore through one of plurality of bores through the first clamp bracket and screwing each of the screws into a threaded bore in the second clamp bracket;

tightening the plurality of screws until an inside surface of the tubular shell engages and starts to apply pressure to the bone; and simultaneously tightening the plurality of screws until the bone is held securely in the first end and the second end of the tubular shell.

12. A tubular splint comprising:
a tubular shell having a first end, a second end and a shell slot extending from the first end to the second end;
a first clamp bracket on said tubular shell adjacent to a first side of the shell slot, and a plurality of bores through the first clamp bracket spaced along a line extending from the first end to the second end of said tubular shell;
a second clamp bracket on said tubular shell adjacent to a second side of the shell slot, and a plurality of threaded bores in the second clamp bracket each of which is in axial alignment with one of the plurality of bores through the first clamp bracket;
a plurality of screws each of which passes through one of the plurality of bores through the first clamp bracket and screws into one of the plurality of threaded bores in the second clamp bracket;
a worm wheel secured to each of the plurality of screws; and
a worm journalled on the first clamp bracket and in mesh with all of the worm wheels.

13. A tubular splint, as set forth in claim 12, wherein the worm is journalled in a worm bore in the first clamp bracket and is axially fixed in the worm bore.

14. A tubular splint, as set forth in claim 13, including a snap ring mounted in a snap ring groove in the worm bore that limits axial movement of the worm in the worm bore.

15. A tubular splint comprising;
a tubular shell having a first end, a second end and a shell slot extending from the first end to the second end;
a first clamp bracket on said tubular shell adjacent to a first side of the shell slot, and a plurality of bores through the first clamp bracket spaced along a line extending from the first end to the second end of said tubular shell;
a second clamp bracket on said tubular shell adjacent to a second side of the shell slot, and a plurality of threaded bores in the second clamp bracket each of which is in axial alignment with one of the plurality of bores through the first clamp bracket;
a plurality of screws each of which passes through one of the plurality of bores through the first clamp bracket and screws into one of the plurality of threaded bores in the second clamp bracket; and
a tubular wedge with a wedge slot, an inside sleeve surface that generally conforms to the shape of a bone and an outside sleeve surface that is engageable by said tubular shell.

* * * * *